United States Patent [19]

Cho et al.

[11] Patent Number: 5,103,034

[45] Date of Patent: Apr. 7, 1992

[54] PROCESS FOR PREPARING ALKOXYSILANES

[75] Inventors: Tsurahide Cho, Tokyo; Yoshiro Ohta, Kawasaki; Osamu Yagi, Kawasaki; Ryuichi Oyama, Kawasaki, all of Japan

[73] Assignee: Tama Chemicals Co., Ltd., Tokyo, Japan

[21] Appl. No.: 671,240

[22] Filed: Mar. 19, 1991

[30] Foreign Application Priority Data

Mar. 23, 1990 [JP] Japan .................................. 2-71998

[51] Int. Cl.$^5$ .......................... C07F 7/04; C07F 7/18
[52] U.S. Cl. ................................................. 556/470
[58] Field of Search ......................................... 556/470

[56] References Cited

U.S. PATENT DOCUMENTS

| | | | |
|---|---|---|---|
| 2,473,260 | 6/1949 | Rochow | 556/470 |
| 3,775,457 | 9/1972 | Muraoka | 556/470 |
| 4,185,029 | 1/1980 | Kreiybury et al. | 556/470 |
| 4,288,604 | 9/1981 | Magee et al. | 556/470 |
| 4,289,889 | 9/1981 | Herdle et al. | 556/470 |
| 4,323,690 | 4/1982 | Moutle et al. | 556/470 |
| 4,487,949 | 12/1984 | Mallon | 556/470 |
| 4,762,439 | 8/1988 | Mendicino | 556/470 |
| 4,931,578 | 6/1990 | Ohta | 556/470 |

FOREIGN PATENT DOCUMENTS

| | | |
|---|---|---|
| 50-34537 | 11/1975 | Japan . |
| 51-118727 | 10/1976 | Japan . |
| 54-44619 | 4/1979 | Japan . |
| 55-26148 | 7/1980 | Japan . |
| 60-4193 | 1/1985 | Japan . |

*Primary Examiner*—Paul F. Shaver
*Attorney, Agent, or Firm*—Armstrong, Nikaido, Marmelstein, Kubovcik & Murray

[57] ABSTRACT

This invention relates to a process for preparing alkoxysilanes of the general formula $(R^2)_a SiH(OR^1)_b$ in which $R^1$ is a lower alkyl group with 1 to 6 carbon atoms, $R^2$ is an aliphatic or aromatic hydrocarbon radical with 1 to 8 carbon atoms, $a$ is 0 or 1, and $b$ is 2 or 3 by the reaction of metallic silicon, an alcohol, and an acetal and/or an orthocarboxylic acid ester in the presence of a copper catalyst and provides a novel process for preparing directly and advantageously alkoxysilanes having one hydrogen atom linked to the silicon atom, particularly alkyldialkoxysilanes and trialkoxysilanes.

6 Claims, No Drawings

PROCESS FOR PREPARING ALKOXYSILANES

FIELD OF THE INVENTION AND RELATED ART STATEMENT

This invention relates to a process for preparing industrially useful alkoxysilanes having one hydrogen atom linked to the silicon atom by the direct reaction of metallic silicon, an alcohol, and an acetal.

Alkyldialkoxysilanes and trialkoxysilanes are known as alkoxysilanes having one hydrogen atom linked to the silicon atom. Due to the presence of a reactive hydrogen atom, the alkoxysilanes in question are extremely useful as intermediates in the preparation of a large number of high-purity silicon compounds, particularly in such end uses as modified silicone sealants, anti-fogging agents, water repellents, silane coupling agents, and coating materials.

A number of processes have been known for the preparation of such alkoxysilanes. An alkyldialkoxysilane (e.g. methyldimethoxysilane) is prepared by the conversion of an alkyltrichlorosilane (e.g. methyltrichlorosilane) to an alkyldichlorosilane (e.g. methyldichlorosilane) followed by the reaction of the alkyldichlorosilane with an alcohol (e.g. methanol) as illustrated below:

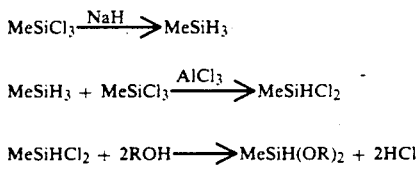

Or, as is disclosed in Japan Tokkyo Koho No. 50-34,537 (1975), an alkylsilane such as methylsilane resulting from the reaction of an alkyltrichlorosilane with sodium hydride is allowed to react with an alcohol such as methyl alcohol in the presence of Wilkinson's catalyst [tris(triphenylphosphine)chlororhodium] as follows:

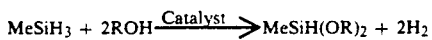

These processes, however, yield alkyldichlorosilanes and alkylsilanes in small quantities, only 3 to 12% by weight based on metallic silicon, and condensation products and other by-products of no commercial value in large quantities. In addition, the process flow is complex and long and suffers from excessive formation of by-products and strict control of the reaction system is required in order to improve the product yield. In the former process, in particular, a large quantity of hydrogen chloride evolves to corrode the reactor in the course of the reaction and this makes it necessary to protect the whole equipment against corrosion by such means as glass lining, thereby incurring large capital cost. Furthermore, the hydrogen chloride thus evolved partly reacts with the alcohol to form water, which then reacts with the product alkyldialkoxysilane and markedly reduces its yield.

Many proposals have also been made on processes for the preparation of trialkoxysilanes, for example, in Japan Tokkyo Kokai Koho Nos. 51-11,721 (1976), 51-118,727 (1976), 54-44,619 (1979), and 60-4,193 (1985) and Japan Tokkyo Koho No. 55-26, 148 (1980). These processes are all based on the reaction of a trichlorosilane with an alcohol and have the same problems as those of the aforesaid alkyldialkoxysilanes.

OBJECT AND SUMMARY OF THE INVENTION

The present inventors have undertaken extensive studies on a process for preparing alkoxysilanes having one hydrogen atom linked to the silicon atom, particularly alkyldialkoxysilanes and trialkoxysilanes, directly and advantageously from metallic silicon, found that the copresence of an acetal and an orthocarboxylic acid ester is beneficial to the preparation of an alkoxysilane by the reaction of metallic silicon and an alcohol in the presence of a copper catalyst, and completed this invention.

It is therefore an object of this invention to provide a novel process for preparing alkoxysilanes having one hydrogen atom linked to the silicon atom, particularly alkyldialkoxysilanes and trialkoxylsilanes, directly and advantageously from metallic silicon.

This invention thus relates to a process for preparing alkoxysilanes of the following general formula (1)

$$(R^2)_a SiH(OR^1)_b \tag{1}$$

in which $R^1$ is a lower alkyl group with 1 to 6 carbon atoms and $R^2$ is an aliphatic or aromatic hydrocarbon radical with 1 to 8 carbon atoms, a is an integer of 0 or 1, and b is an integer of 2 or 3 by the reaction of metallic silicon, an alcohol, and an acetal and/or an orthocarboxylic acid ester and, more specifically, to a process for preparing alkoxysilanes, particularly alkyldialkoxysilanes and trialkoxysilanes, wherein said alkoxysilanes of the general formula (1) are represented by the following general formula (2) and/or (3)

$$R^2 SiH(OR^1)_2 \tag{2}$$

$$HSi(OR^1)_3 \tag{3}$$

in which $R^1$ and $R^2$ are as defined above.

Metallic silicon to be used as raw material in the process of this invention is required to be 80% by weight or more in purity and 200 mesh or less in average particle diameter. A commercial material with a purity of 80 to 99% by weight and an average particle diameter of 50 to 100 mesh prepared by such means as an oscillating mill and a ball mill may be used as sold. It is preferable to grind metallic silicon with a purity of 98% or higher and an average particle diameter of 1 to 3 mm further to 300 mesh or less in a grinder such as a ball mill before use. Metallic silicon occasionally contains metals such as Fe, Ca, Mg, Zn, Al, Ti, Cr, Ni, Mn, Ba, Cu, and Zr in varying amounts of 1% by weight or so to several ppm, but their presence produces no ill effect.

The raw material alcohols are normally alkanols, preferably lower alkanols with 1 to 6 carbon atoms such as methyl alcohol, ethyl alcohol, n-propyl alcohol, isopropyl alcohol, n-butyl alcohol, isobutyl alcohol, and amyl alcohol. The alcohols should have a purity of 98% by weight or more, preferably 99.9% by weight or more, and a water content of 0.2% by weight or less, preferably 0.1% by weight or less. The alcohol is used normally at a rate of 3 to 10 moles per 1 mole of metallic silicon, preferably 4 to 8 moles in order to enhance the conversion of metallic silicon.

The acetals to be used in this invention include dimethoxymethane, diethoxymethane, dimethoxyethane, diethoxyethane, 2,2-dimethoxypropane, 2,2-dimethoxybutane, 2,2-dimethoxypropane, 2,2-diethoxybutane, 1,1-diethoxypropane, (1,1-dimethoxybutyl)benzene, 2,2-dimethoxypentane, ethylidene dimethyl ether, ethylidene diethyl ether, chloroacetal, trichloroacetal, and bromoacetal. The acetals should have a purity of 90% by weight or more, preferably 95% by weight or more, and a water content of 0.2% by weight or less, preferably 0.1% by weight or less. The acetal is used normally at a rate of 3 to 10 moles per 1 mole of metallic silicon, preferably 4 to 8 moles in order to enhance the conversion of metallic silicon.

The orthocarboxylic acid esters to be use in place of or together with the acetals include trimethyl orthoformate, triethyl orthoformate, trimethyl orthoacetate, and triethyl orthoacetate. The orthocarboxylic acid ester should have a purity of 90% by weight or more, preferably 95% by weight or more, and a water content of 0.2% by weight or less, preferably 0.1% by weight or less, and is used normally at a rate of 3 ot 10 moles, preferably 4 to 8 mole, per 1 mole of metallic silicon. In case of the simultaneous use of orthocarboxylic acid ester and acetal, the combined amount of 3 to 10 moles is used per 1 mole of metallic silicon.

It is desirable that the aforesaid alcohol and the acetal and/or the orthocarboxylic acid ester are mixed at a weight ratio of 2:1 to 1:2 and introduced continuously into the reaction system.

The known copper catalysts may be used in the process of this invention and include metallic copper powders and copper compounds such as cuprous chloride, cupric chloride, cuprous bromide, cupric bromide, cuprous iodide, cupric iodide, copper formate, copper acetylacetonate, cuprous acetate, cupric acetate, cuprous oxide, and cupric oxide. The metallic copper powders and the copper compounds may be used singly or in combination of two or more at a rate of 0.005 to 0.5 mole, preferably 0.01 to 0.1 mole, per 1 mole of metallic silicon. Less than 0.005 mole of the copper catalyst will lower the conversion of metallic silicon while more than 0.5 mole will not improve the conversion of metallic silicon and the selectivity of alkyldialkoxysilanes any further and hence will rather be uneconomical.

The copper catalyst is preferably activated before use by heating it with the pulverized metallic silicon in the vapor or liquid phase at 200° to 400° C. in the presence of a specified amount of an organic halide.

It is advisable in the process of this invention to add a halide to the reaction system as a stabilizer for the reaction products, namely alkyldialkoxysilanes and trialkoxysilanes, during the reaction of the aforesaid metallic silicon, an alcohol, and an acetal and/or an orthocarboxylic acid ester in the presence of a copper catalyst.

The halide to be introduced into the reaction system for the above-mentioned purpose may be organic or inorganic. Organic halides are preferable and include alkyl halides such as methyl chloride, methyl bromide, methyl fluoride, methyl iodide, dichloromethane, chloroform, carbon tetrachloride, ethyl chloride, ethyl bromide, ethyl fluoride, ethyl iodide, dichloroethane, n-propyl chloride, n-propyl bromide, n-propyl fluoride, and n-propyl iodide, aryl halides such as chlorobenzene and dichlorobenzene, and organic acid halides such as acetic acid chloride. Inorganic halides include hydrogen halides such as hydrogen chloride, hydrogen bromide, hydrogen fluoride, and hydrogen iodide, ammonium halides such as ammonium chloride, ammonium bromide, ammonium fluoride, and ammonium iodide, trimethylamine hydrochloride, trimethylamine hydrobromide, triethylamine hydrochloride, triethylamine hydrobromide, tetramethylammonium chloride, tetramethylammonium bromide, choline chloride, and choline bromide. These halides may be used singly or in a mixture of two or more.

The halide is used at a rate of 0.0001 to 1 mole, preferably 0.001 to 0.5 mole, per 1 mole of metallic silicon. With less than 0.0001 mole of the halide, the metallic silicon and the copper catalyst will not be activated sufficiently and alkali metals and alkaline earth metals present as impurities in the metallic silicon will form alcoholates, which will turn the reaction system alkaline and lower the selectivity of alkyldialkoxysilanes and/or trialkoxysilanes. On the other hand, more than 1 mole of the halide will enhance the acidity too much resulting in lowered selectivity of alkyldialkoxysilanes and/or trialkoxysilanes and besides it will be uneconomical.

The halide may be used straight or, for better control of the addition or easier handling, it may be diluted with an inert gas such as nitrogen or with hydrogen or dissolved in an alcohol, an acetal, or an orthocarboxylic acid ester and introduced into the reaction system.

The reaction may be carried out in either the vapor phase or the liquid phase in the process of this invention, preferably in the liquid phase for more uniform and precise control of the temperature in the reaction system. Any solvent may be used satisfactorily in the reaction as long as it is stable in the reaction system and can be heated up to the specified reaction temperature. A variety of hydrocarbons are useful; for example, paraffins such as octane, decane, dodecane, tetradecane, hexadecane, octadecane, and eicosane, alkylbenzenes such as ethylbenzene, trimethylbenzene, cymene, diethylbenzene, butylbenzene, butyltoluene, octylbenzene, dodecylbenzene, and didodecylbenzene, hydrogenation products of alkylbenzenes, biphenyl derivatives such as biphenyl, diphenyl ether, monoethylbiphenyl, diethylbiphenyl, and triethylbiphenyl, hydrogenation products of biphenyl derivatives, alkylnaphthalenes and their hydrogenation products, and terphenyls and their hydrogenation products. Such solvents may be used singly or in a combination of two or more. Preferably among them are those which do not foam during the reaction and boil at 100° to 500° C., preferably at 200° to 400° C., under atmospheric pressure. The solvent to be used for the activation of the metallic silicon and the copper catalyst and the one for the reaction of the metallic silicon, an alcohol, and an acetal and/or an orthocarboxylic acid ester may be different from each other, but they should preferably be identical because of the desirability of carrying out the activation and the reaction continuously.

In the reaction of this invention, the reaction system is preferably maintained in an atmosphere of an inert gas such as nitrogen or of hydrogen and the acidity inside the reaction system and of the product distilled from the reaction system is controlled at pH 1 to 6, preferably 2 to 4.

The process of this invention produces a considerable amount of tetraalkoxysilanes and alkyltrialkoxysilanes as by-products. One feature of this invention is that these by-products are themselves useful as components for paints, investment foundry resins, and a variety of coating materials and as raw materials for silica sealants for integrated circuits, quartz, and optical fibers.

An acetal and/or an orthocarboxylic acid ester co-present in the system participates in the reaction to form the desired products. This is illustrated below for the reaction of silicon, methanol as an alcohol, and dimethoxymethane (methylal) as an acetal to yield methyltrimethoxysilane and trimethoxysilane:

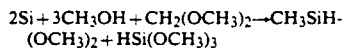

$$2Si + 3CH_3OH + CH_2(OCH_3)_2 \rightarrow CH_3SiH(OCH_3)_2 + HSi(OCH_3)_3$$

As a result, the yield of useful compounds, alkyldialkoxysilanes and/or trialkoxysilanes, improves markedly compared with that in the absence of these additives.

According to the process of this invention, the direct reaction of metallic silicon, an alcohol, and an acetal and/or an orthocarboxylic acid ester advantageously yields a variety of commercially valuable alkoxysilanes, particularly alkyldialkoxysilanes and trialkoxysilanes.

DETAILED DESCRIPTION OF THE PREFERRED EMBODIMENT

This invention will be explained in detail below with reference to the accompanying examples and comparative examples.

EXAMPLES 1-3

A copper reactor equipped with a stirrer was fitted with an inlet tube for alcohol and acetal, an inlet tube for nitrogen and halide, a product distilling tube, and a thermometer, 400 g. of metallic silicon with a purity of 98% by weight (determined by ICP emission spectrometry: Fe 0.83 wt. %, Ca 0.35 wt. %, Mg 150 ppm, Zn 320 ppm, Al 0.60 wt. %, Ti 860 ppm, Cr 40 ppm, Ni 43 ppm, Mn 240 ppm, Ba 50 ppm, Cu 32 ppm, and Zr 180 ppm) pulverized to an average particle diameter of about 200 mesh or less, 900 ml. of an alkylbenzene-based hydrocarbon boiling at 280° to 300° C. (available from Mitsubishi Petrochemical Co., Ltd. under the tradename of AB-HL), and 20 g. of cuprous chloride were introduced into the reactor, and the distilling tube for the products was fitted with a condenser at the outlet.

The contents were heated to 220° to 240° C. over 3 to 4 hours with stirring by introducing nitrogen into the reactor at a flow rate of 20 to 30 ml./min., then methyl chloride (gas) was introduced at a rate of 20 to 30 ml./min. at 220° to 240° C. for 3 to 4 hours, the introduction of the methyl chloride was stopped, and the reaction mixture was aged at 220° to 240° C. for 3 to 4 hours by introducing nitrogen at a flow rate of 20 to 30 ml./min.

The metallic silicon and the cuprous chloride were thus activated, a 1:1 mixture by volume of methyl alcohol with a purity of 99.9% by weight or more and methylal with a purity of 99.0% by weight or more was introduced into the reactor through the inlet tube for alcohol and acetal at a rate of 30 to 35 g./hr., methyl chloride (gas) was simultaneously introduced into the reactor through the inlet tube for halide at a rate of 20 to 30 ml./min., the reaction was allowed to proceed at 200° to 260° C. for 90 to 100 hours, and the reaction products flowing out of the product distilling tube were collected.

The reaction products thus obtained were analyzed by gas chromatography for trimethoxysilane (Tr-MeS), tetramethoxysilane (Te-MeS), methyldimethoxysilane (MDiMeS), and methyltrimethoxysilane (MTrMeS). The results are shown in Table 1.

COMPARATIVE EXAMPLE 1

The reaction was carried out as in the above-mentioned Examples except introducing only methyl alcohol, taken from the same lot as in Examples 1 to 3, into the reactor through the inlet tube for alcohol and acetal and the reaction products were analyzed by gas chromatography. The reaction conditions and the results are shown in Table 1.

TABLE 1

|  |  | Example |  |  | Comparative example |
|---|---|---|---|---|---|
|  |  | 1 | 2 | 3 | 1 |
| Reactant feed rate (g./hr.) |  | 32.8 | 33.8 | 31.7 | 32.6 |
| Reaction temperature (°C.) |  | 210–222 | 251–260 | 248–263 | 201–238 |
| CH$_3$Cl feed rate (ml./min.) |  | 20 | 30 | 30 | 20 |
| Analysis of reaction | Tr-Mes | 33.3 | 34.0 | 40.4 | 44.2 |
| products by gas | Te-Mes | 29.4 | 33.8 | 28.7 | 47.4 |
| chromatography | MDiMeS | 8.2 | 15.7 | 17.7 | 1.6 |
| (area, %) | MTrMeS | 19.1 | 15.7 | 13.1 | 6.8 |
| Selectivity of MDiMeS and Tr-MeS (*1) |  | 27.3 | 31.4 | 30.9 | 8.4 |
| Conversion of Si (%) (*2) |  | 20.1 | 26.3 | 28.7 | 10.4 |
|  |  | 55.1 | 61.3 | 63.7 | 20.4 |

(Notes)
(*1): Selectivity of MDiMeS and Tr-MeS (%) =
$$\frac{\{DiMeS\,(\%) + Tr\text{-}MeS\,(\%)\}}{\{Tr\text{-}MeS\,(\%) + Te\text{-}Mes\,(\%) + MDiMeS\,(\%) + MTrMeS\,(\%)\}} \times 100$$
(*2): Upper column; 3 to 5 hours after feeding of the reactants Lower column; final

EXAMPLES 4-6

The reaction was carried out for 50 to 60 hours by placing 400 g. of metallic silicon and 900 ml. of an alkylbenzene-base hydrocarbon, both taken from the same lots as in Example 1, and 20 g. of metallic copper with an average particle diameter of 100 mesh in the same reactor as that in Example 1, maintaining the reactor at 170° to 240° C., introducing a 5:5:1 mixture of methyl alcohol with a purity of 99.9% by weight or more, methylal with a purity of 99.0% by weight or more, and dichloromethane with a purity of approximately 99% by weight or more at a rate of 50 to 55 g./hr., and recovering the reaction products emerging from the product distilling tube. The products were analyzed as in Examples 1 to 3. The results are shown in Table 2.

COMPARATIVE EXAMPLE 2

The reaction was carried out as in Examples 4 to 6 except introducing only the methyl alcohol through the inlet tube for alcohol and acetal into the reactor and the reaction products were analyzed by gas chromatography. The reaction conditions and the results are shown in Table 2.

TABLE 2

|  | Example | | | Comparative example |
|---|---|---|---|---|
|  | 4 | 5 | 6 | 2 |
| Reactant feed rate (g./hr.) | 53.9 | 55.2 | 49.4 | 54.4 |
| Reaction temperature (°C.) | 172–182 | 170–190 | 225–237 | 181–238 |
| $N_2$ feed rate (ml./min.) | 20 | 20 | 20 | 20 |
| Analysis of reaction products by gas chromatography (area, %) | | | | |
| Tr-MeS | 49.9 | 59.0 | 33.6 | 83.9 |
| Te-MeS | 40.8 | 30.9 | 47.4 | 12.4 |
| MDiMeS | 7.7 | 8.5 | 7.2 | 3.5 |
| MTrMeS | 1.5 | 1.7 | 11.7 | 0.2 |
| Selectivity of MDiMeS and Tr-MeS[*1] | 9.4 | 10.1 | 19.0 | 3.7 |
| Conversion of Si (%)[*2] | 33.2 | 46.8 | 74.2 | 14.5 |
|  | 68.2 | 81.8 | 84.2 | 24.5 |

(Notes)
[*1]Same as in Table 1
[*2]Same as in Table 1

EXAMPLES 7 AND 8

A reactor was set up as in Example 1 using a four-necked flask and the catalyst was activated by placing 80 g. of metallic silicon from the same lot as in Example 1, 160 ml. of tricyclic hydrocarbon (available from Nippon Oil Co., Ltd. under the tradename of Hisol SAS-LH) boiling at 350° to 400° C., and 4 g. of cuprous chloride and heating the mixture to 240° C. over 3 hours while blowing in methyl chloride (gas) at a flow rate of 15 ml./min.

A 1:1 mixture by volume of methyl alcohol and methylal, both taken from the same lots as in Example 1, was introduced at a rate of 50 to 60 g./hr. and simultaneously methyl chloride (gas) was introduced at a flow rate of 15 ml./min into the reactor which was kept at 260° to 310° C., the reaction was allowed to proceed for about 10 hours, and the reaction products emerging from the product distilling tube were recovered. The products were analyzed as in Example 1. The results are shown in Table 3.

EXAMPLES 9 AND 10

Into a reactor set up as in Example 7 were introduced 80 g. of metallic silicon and 160 ml. of alkylbenzene-based hydrocarbon, both taken from the same lots as in Example 1, and 4 g. of cuprous chloride, the contents in the reactor were heated at 240° C., a 1:1 mixture by volume of methyl alcohol, taken from the same lot as in Example 1, and 2,2-dimethoxypropane with a purity of 95% by weight or more was introduced at a rate of 50 to 60 g./hr., methyl chloride (gas) was simultaneously introduced at a flow rate of 15 ml./min., the reaction was allowed to proceed for about 10 hours, and the reaction products emerging from the product distilling tube were recovered. The products were analyzed as in Example 1. The results are shown in Table 3.

EXAMPLE 11

The reaction was carried out as in Example 7 except using trimethyl orthoformate in place of 2,2-dimethoxypropane and the reaction products were recovered and analyzed as in Example 1. The results are shown in Table 3.

TABLE 3

|  | Example | | | | |
|---|---|---|---|---|---|
|  | 7 | 8 | 9 | 10 | 11 |
| Reactant feed rate (g./hr.) | 53.1 | 53.1 | 55.8 | 52.8 | 60.9 |
| Reaction temperature (°C.) | 260–286 | 298–310 | 239–241 | 237–241 | 239–241 |
| $CH_3Cl$ feed rate (ml./min.) | 15 | 15 | 15 | 15 | 15 |
| Analysis of reaction products by gas chromatography (area, %) | | | | | |
| Tr-MeS | 49.2 | 64.5 | 76.4 | 81.4 | 69.0 |
| Te-MeS | 16.6 | 11.4 | 6.3 | 5.7 | 6.7 |
| MDiMeS | 18.1 | 23.1 | 13.1 | 6.7 | 24.3 |
| MTrMeS | 16.0 | 1.0 | 4.2 | 6.2 | — |
| Selectivity of MDiMeS and Tr-MeS[*1] | 34.1 | 24.1 | 17.3 | 12.8 | 24.3 |
| Conversion of Si (%)[*2] | 11.6 | 22.8 | 26.0 | 56.5 | 39.3 |
|  | 46.6 | 57.8 | 61.0 | 76.5 | 39.2 |

(Notes)
[*1]Same as in Table 1
[*2]Same as in Table 1

What is claimed is:

1. A process for preparing alkoxysilanes of the following general formula (1)

$$(R^2)_a SiH(OR^1)_b \qquad (1)$$

in which $R^1$ is a lower alkyl group with 1 to 6 carbon atoms, $R^2$ is an aliphatic or aromatic hydrocarbon radical with 1 to 8 carbon atoms, a is an integer of 0 or 1, and b is an integer of 2 to 3 characterized by allowing metallic silicon, an alcohol, and an acetal and/or an orthocarboxylic acid ester to react in the presence of a copper catalyst.

2. A process for preparing alkoxysilanes according to claim 1 wherein said alkoxysilanes of the general formula (1) are alkyldialkoxysilanes of the following general formula (2) or trialkoxysilanes of the following general formula (3)

$$R^2SiH(OR^1)_2 \qquad (2)$$

$$HSi(OR^1)_3 \qquad (3)$$

in which $R^1$ is a lower alkyl group with 1 to 6 carbon atoms and $R^2$ is an aliphatic or aromatic hydrocarbon radical with 1 to 8 carbon atoms.

3. A process for preparing alkoxysilanes according to claim 1 or 2 wherein the reaction is carried out in the liquid phase by using an aliphatic or aromatic hydrocarbon with a boiling point of 100° to 400° C. at ambient pressure as reaction solvent.

4. A process for preparing alkoxysilanes according to claim 1 or 2 wherein said alcohol is methanol or ethanol and said acetal is methylal or ethylal.

5. A process for preparing alkoxysilanes according to claim 1 or 2 wherein said alcohol is methanol or ethanol and said orthocarboxylic acid ester is trimethyl orthoformate or triethyl orthoformate.

6. A process for preparing alkoxysilanes according to claim 1 or 2 wherein a halide is made to be present in said reaction of metallic silicon, an alcohol, and an acetal and/or an orthocarboxylic acid ester in the presence of a copper catalyst.

* * * * *